United States Patent [19]

Engelbrecht et al.

[11] Patent Number: 5,026,399
[45] Date of Patent: Jun. 25, 1991

[54] PROSTHETIC DEVICE

[75] Inventors: Eckart Engelbrecht, Hamburg; Elmar Nieder, Jork; Arnold Keller, Kaihude, all of Fed. Rep. of Germany

[73] Assignees: GMT Gesellschaft fur Medizinsche Texhnik mbH; Waldemar Link GmbH & Co., both of Hamburg, Fed. Rep. of Germany

[21] Appl. No.: 766,072

[22] Filed: Aug. 14, 1985

Related U.S. Application Data

[63] Continuation of Ser. No. 423,080, Sep. 24, 1982, abandoned.

[30] Foreign Application Priority Data

Sep. 30, 1981 [DE] Fed. Rep. of Germany ....... 3138848

[51] Int. Cl.$^5$ ............................ A61F 2/30; A61F 2/34
[52] U.S. Cl. ........................................ 623/18; 623/23
[58] Field of Search ..................... 623/16–23

[56] References Cited

U.S. PATENT DOCUMENTS

| | | | |
|---|---|---|---|
| 1,236,145 | 8/1917 | Burns | 403/360 |
| 3,067,740 | 12/1962 | Haboush | 128/92 |
| 3,170,691 | 2/1965 | Pritchard | 403/296 |
| 3,748,662 | 7/1973 | Helfet | 623/21 |
| 3,894,297 | 7/1975 | Mittelmeier et al. | 623/23 |
| 4,051,559 | 10/1977 | Pifferi | 128/92 C |
| 4,187,559 | 2/1980 | Grell et al. | 623/21 |
| 4,404,691 | 9/1983 | Buning et al. | 623/23 |

FOREIGN PATENT DOCUMENTS 2839093 3/1980 Fed. Rep. of Germany ........ 623/23

OTHER PUBLICATIONS

Zimmer, "Specifications of Zimmer Implant Metals", catalogue A1, Dec. 1983.

*Primary Examiner*—David J. Isabella
*Attorney, Agent, or Firm*—Peter K. Kontler

[57] ABSTRACT

An internal prosthesis for the partial or total replacement of a bone such as a femur has a rod-like bridging member which spans the major part of the gap between two joints. An abutment member is mounted at either end of the bridging member and each of the abutment members engages a bone adjacent that which is to be partially or totally replaced. Each of the abutment members may constitute part of an artificial joint. The bridging member and/or the abutment members are adjustable so that the prosthesis may be fitted to the particular physical characteristics of a patient. To this end, the bridging member may be composed of sections for the purpose of length adjustment. The abutment members may be rotatable relative to one another and to the bridging member about the longitudinal axis of the latter in order that the abutment members may assume a relative angular orientation best suited to the characteristics of the patient.

6 Claims, 3 Drawing Sheets

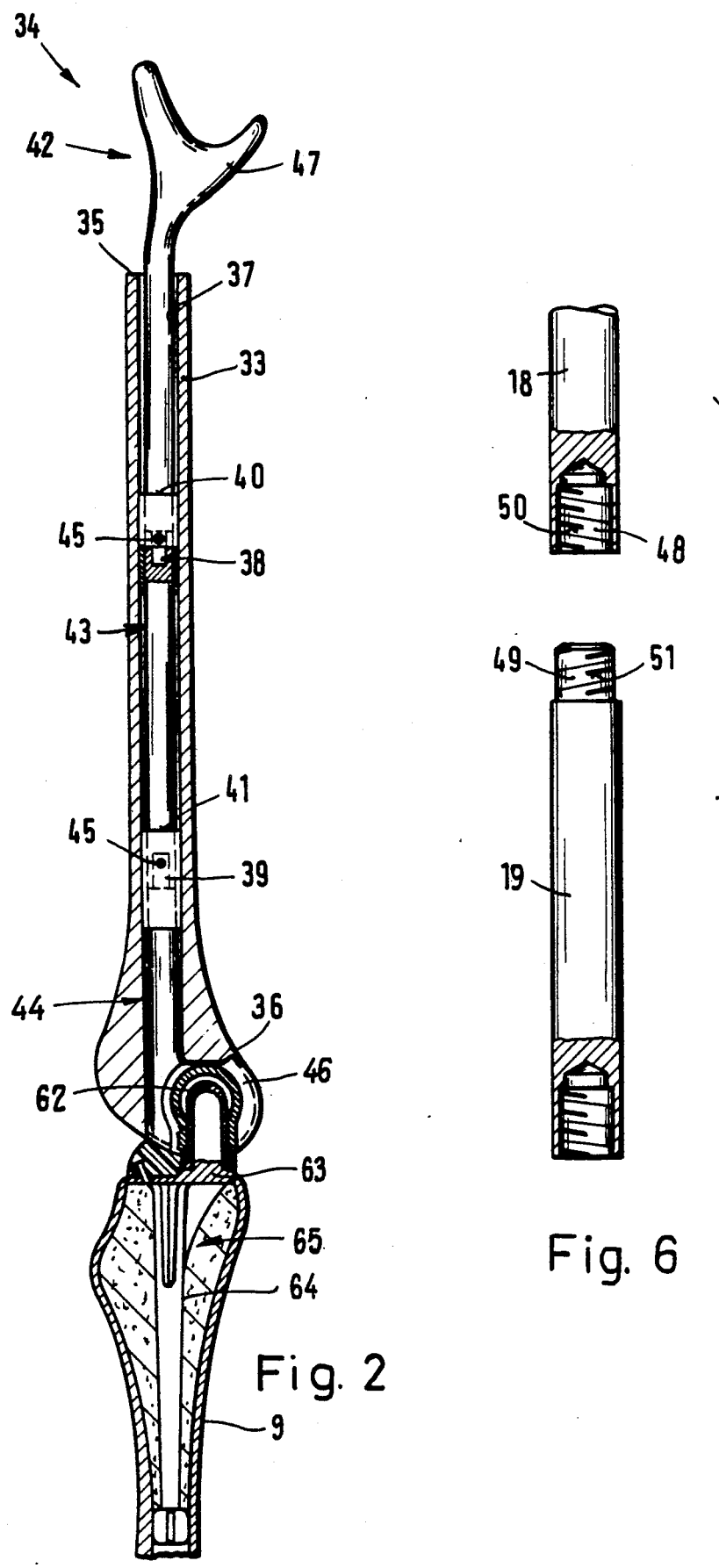

PROSTHETIC DEVICE

This application is a continuation of application Ser. No. 423,080, filed Sept. 24, 1982, now abandoned.

BACKGROUND OF THE INVENTION

The invention relates generally to a prosthesis.

More particularly, the invention relates to an internal prosthesis for the total or partial replacement of a bone.

A known type of prosthesis for the partial replacement of a bone consists of a rod-like member which is provided with an abutment member at one end thereof. The rod-like member is embedded in the bone which is to be partially replaced while the abutment member bears against an adjacent bone.

This type of prosthesis is used when one end of a bone is defective and the other end is healthy. The prosthesis is embedded in the bone to a distance which depends upon the physical characteristics of the patient. In this manner, account is taken of the fact that the distance to be bridged by the prosthesis is different for different patients.

A known prosthesis for the replacement of an entire bone, e.g., for the total replacement of a femur, has a rod-like member which is provided with an abutment member at either end. Each of the abutment members bears against one of the bones which is located adjacent to the bone being replaced. The length of the prosthesis must be such that the distance between the bones engaged by the abutment members remains substantially unchanged from before. The reason is that changes in this distance generally cause discomfort to the patient. For instance, an improperly dimensioned replacement for the femur can cause one leg of the patient to be longer than the other.

Occasionally, difficulties arise with the preoperative measurements required to establish the length of the prosthesis. Consequently, errors in measurement cannot always be avoided. In extreme cases, the errors may be so large that the prosthesis cannot be implanted and a new prosthesis must be constructed.

In some cases, a bone has defects at both its proximal and distal ends but not in the middle. While it is desirable to retain the middle part of the bone, this part of the bone is frequently so short that it is not possible to secure a prosthesis thereto. Accordingly, the entire bone must be replaced by a prosthesis.

OBJECTS AND SUMMARY OF THE INVENTION

It is an object of the invention to provide a prosthesis which makes it possible to minimize discomfort to the patient.

Another object of the invention is to provide a prosthesis which makes it possible to adjust for errors in preoperative measurements.

An additional object of the invention is to provide a prosthesis which is capable of conforming to the physical characteristics of a patient.

A concomitant object of the invention is to provide a prosthesis which enables even short lengths of bone to be retained.

It is also an object of the invention to improve a prosthesis of the type outlined above in such a manner that difficulties in implantation caused by errors in preoperative measurements may be eliminated.

A further object of the invention is to improve a prosthesis of the type outlined above in such a manner that even short lengths of bone with proximal and distal defects may be retained.

The preceding objects, as well as others which will become apparent as the description proceeds, are achieved by the invention.

One aspect of the invention resides in a prosthesis, especially an internal prosthesis for the partial or total replacement of a rod-like bone. The prosthesis comprises a bridging member designed to span at least part of the gap between two joints of the anatomy. The prosthesis also includes an abutment member which is mounted on the bridging member and is designed to connect the bridging member with a component of the anatomy. At least one of these members is adjustable in such a manner as to enable the prosthesis to conform to the different physical characteristics of different anatomies.

The bridging member may have a rod-like configuration.

The adjustability of at least one of the members makes it possible to precisely conform the prosthesis to the individual requirements of the patient while the operation for implanting the prosthesis is being performed. Precise adjustment of the prosthesis to the patient prior to the operation can be extremely difficult since the x-rays used for measurement purposes reproduce the distances between various components of the anatomy relatively imprecisely. The prosthesis according to the invention may be adjusted to the particular characteristics of the patient without a substantial increase in operating time.

By appropriate dimensioning and shaping of the bridging and abutment members, fine adjustment of the length as well as the orientation of the prosthesis are possible.

The shape of the abutment member may be varied to suit particular applications.

The bridging member may be composed of a plurality of rod-like sections. The different sections may be connected to one another by means of cooperating coupling elements provided on adjacent ones of the sections.

The sections may be so designed by a surgeon that the junctions are situated at locations which are particularly favorable for the performance of the operation. For example, when a large defect is present in a bone, it may be desirable to pass the bridging member through the bone in axial direction of the latter and to then connect an abutment member with either end of the bridging member. In such a case, the bridging member is advantageously designed so that the portion thereof inside the bone is of one piece and the junctions between the sections of the bridging member, as well as the junctions between the bridging member and the abutment members, are all located externally of the bone.

By passing the prosthesis through a bone in the above manner, the bone is provided with an internal splint. Furthermore, the forces which would normally be carried by the bone may now be readily carried by the prosthesis. This technique is of particular advantage when biomechanical considerations indicate that it is not possible to connect the defective bone to the adjacent bones by securing a partial prosthesis to either end of the defective bone. By way of example, if a femur is defective to the extent that it cannot be connected to the hip and knee joints via partial prostheses secured to opposite ends thereof, the invention permits a full prosthesis to be passed through the healthy portion of the femur and to be connected both to the hip joint and the knee joint.

The technique of passing a full prosthesis through a defective bone makes it possible to retain all that part of the bone which has not been destroyed by infection, trauma, tumors and so on. This enables the implanted prosthesis to be surrounded by bone to the greatest extent possible. Moreover, the retention of healthy bone is advantageous since such bone provides attachment points for tendons and muscles. In addition, if a defective bone includes a part of a joint which is capable of being saved, such part may be utilized for the performance of its normal function. It is especially favorable to retain the bearing at the patella when a prosthesis is passed through a femur in accordance with the invention.

Precise adjustment of the prosthesis to the particular characteristics of a patient is facilitated by designing the prosthesis so that the abutment member is adjustable relative to the bridging member. In the event that the prosthesis has two abutment members, these may be individually adjustable relative to the bridging member so that the abutment members may be arranged at different angles relative to one another. Such adjustability is of considerable importance in view of the differences which exist between patients.

As indicated previously, the abutment member or members may have various configurations depending upon the particular requirements. For instance, in the case of a full prosthesis for the femur, the proximal abutment member may include a ball or a saddle-shaped portion which engages the pelvis while the distal abutment member includes a knee joint capable of rotating about a horizontal or a vertical axis.

The novel features which are considered as characteristic of the invention are set forth in particular in the appended claims. The improved prosthesis itself, however, both as to its construction and its mode of operation, together with additional features and advantages thereof, will be best understood upon perusal of the following detailed description of certain specific embodiments with reference to the accompanying drawings.

BRIEF DESCRIPTION OF THE DRAWINGS

FIG. 2 is a side view of another embodiment of a prosthesis according to the invention;

FIG. 6 is a partly sectional view illustrating an additional embodiment of cooperating coupling elements.

DESCRIPTION OF THE PREFERRED EMBODIMENTS

Figure 1:
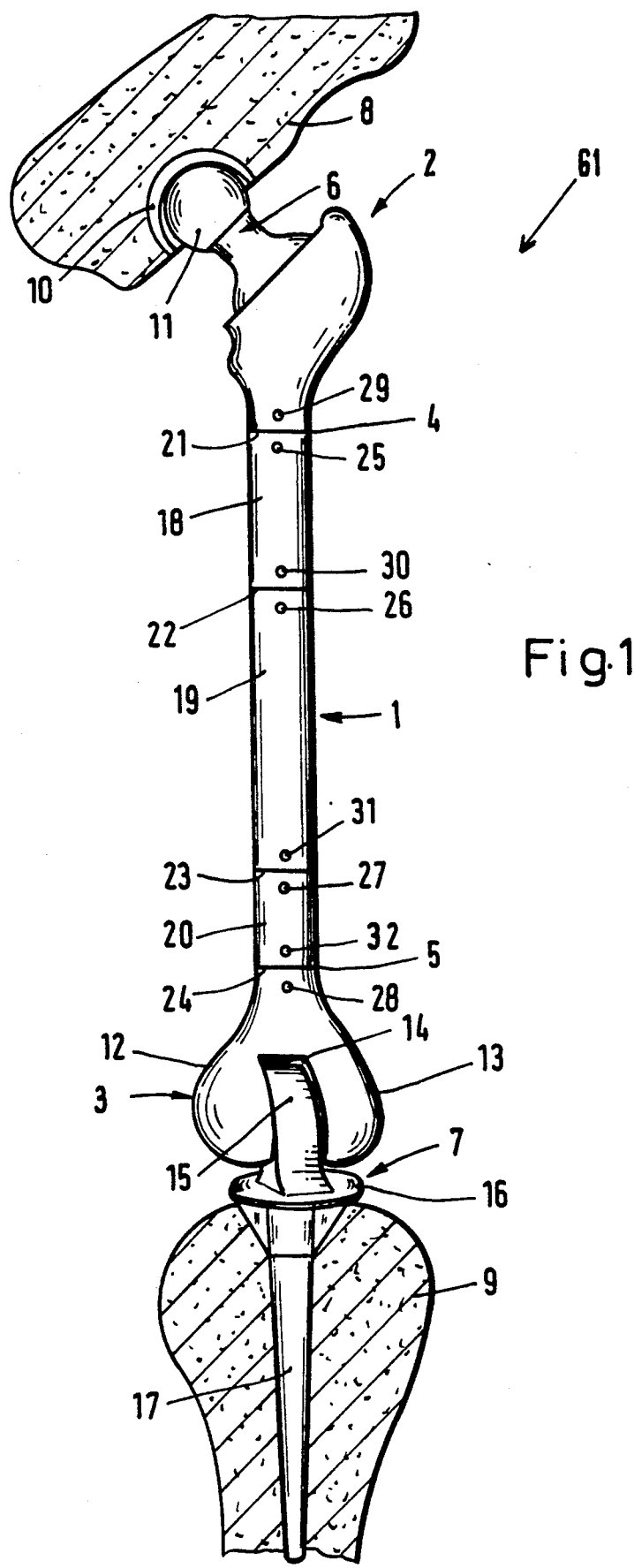
FIG. 1 is a front view of one embodiment of a prosthesis in accordance with the invention.

In FIG. 1, a prosthesis according to the invention is identified generally by the reference numeral 61. The prosthesis 61 includes a rod-shaped bridging member 1 having a pair of opposite axial ends 4 and 5. An abutment member 2 is secured to the end 4 of the bridging member 1 while an abutment member 3 is secured to the end 5 of the bridging member 1. The abutment members 2 and 3 constitute bearings which pivotally or rotatably connect the bridging member 1 to a pelvis 8 and a bone 9 of a lower leg, respectively.

The abutment member 2 has a bearing element 6 which constitutes part of an artificial hip joint. The artificial hip joint comprises an artificial socket 10 which is secured to the pelvis 8 and a ball or part-spherical element 11 which is mounted on the bearing element 6. The ball 11 rides in and intimately mates with the socket 10.

The abutment member 3, which is located in the region of the knee joint, defines a hinge which permits relative pivotal movement of the prosthesis 61 and the bone 9 about a horizontal axis. The abutment member 3 is formed with a pair of enlarged, lateral mounting portions 12 and 13 which are separated by a slot 14. A non-illustrated, horizontal pivot bridges the slot 14 and is supported by the mounting portions 12 and 13. A bearing element 15 is received in the slot 14 and is rotatably mounted on the pivot.

The bone 9 is provided with a prosthesis 7 which may be of a conventional type. The prosthesis 7 includes a shaft 17 which extends into the bone 9 and carries a platform 16 at its upper end. The bearing element 15 of the prosthesis 61 is supported by the platform 16 of the prosthesis 7.

The bridging member 1 is composed of several rod-like sections 18, 19 and 20 having different lengths. The sections 18-20 are separably connected to one another and to the abutment members 2 and 3 by means of plug-and-socket type connections 21, 22, 23 and 24. All of the plug-and-socket type connections 21-24 are identical. With reference to the plug-and-socket type connection 22, one of the sections 18 and 19 is provided with an axially extending opening while the other is provided with an axially extending plug or projection which is received in the opening. In order to prevent relative rotation of the abutment members 2, 3 and the sections 18-20, aligned transverse passages are provided in the plugs and in the respective portions of the abutment members 2, 3 and sections 18-20 which circumscribe the plugs. Pins 25, 26, 27 and 28 are received in the aligned passages to fix the abutment members 2, 3 and sections 18-20 against relative rotation. The lengths of the pins 25-28 should be no greater than the diameter of the bridging member 1 to prevent the pins 25-28 from projecting out of the respective passages.

Another manner of joining the abutment members 2, 3 and sections 18-20 will be described with reference to the sections 18 and 19. Instead of the plug-and-socket type connection 22 in which one of the sections 18 and 19 is provided with an axially extending opening while the other is provided with a mating plug or projection, each of the sections 18 and 19 may be provided with an axially extending opening. The two openings cooperate to define an axially extending recess, and an axially extending peg is placed inside the recess. The portions of the sections 18 and 19 which circumscribe the peg are provided with transverse passages and these passages are aligned with a pair of corresponding transverse passages provided in the peg. The pin 26 is inserted into one set of aligned passages while an additional pin 30 is inserted through the other set of aligned passages. Additional pins 29, 31 and 32 similar to the additional pin 30 are provided at the junction between the abutment member 2 and the section 18, the junction between the sections 19, 20, and the junction between the section 20 and the abutment member 3. This manner of joining the abutment members 2, 3 and the sections 18-20 has the advantage that the number of ways in which the sections 18-20 may be combined is increased.

The sections 18-20 may be prefabricated in such a manner that it is only necessary to connect these to one another and to the abutment members 2, 3 during the operation. In many cases, however, this will not be possible and a length adjustment may be required during the operation. Adjustment of the length of the prosthesis 61 may be undertaken by installing or removing one or more short sections such as the section 20 which are provided for this purpose.

It will be observed that the prosthesis 61 is an internal prosthesis for total replacement of the femur.

The prosthesis 61 is designed to be inserted in place of the femur once the latter has been removed. In contrast, FIG. 2 illustrates a prosthesis 34 which is designed to be mounted in a defective bone 33. Frequently, it is not possible to secure partial prostheses to the ends 35 and 36 of the bone 33 in order to transmit forces into the bone 33. The reason is that the defect or defects in the bone 33 are such that the latter is no longer capable of withstanding the forces which must be transmitted through it without undergoing further destruction.

The prosthesis 34 includes a bridging member 43 as well as a pair of abutment members 42 and 44. The abutment members 42 and 44 are connected to the bridging member 43 by means of plug-and-socket type connections 38 and 39. In order to prevent relative rotation of the members 42-44, aligned transverse passages are formed in the plugs and the corresponding portions of the members 42-44 which circumscribe the plugs. A sleeve 40 is fitted over the plug-and-socket type connection 38 and has transverse passages which are designed to register with the aligned passages of the members 42 and 43. Similarly, a sleeve 41 is fitted over the plug-and-socket type connection 39 and is provided with transverse passages which are designed to register with the aligned passages in the members 43 and 44. Pins 45 are inserted in the sets of aligned passages to fix the members 42-44 against relative rotation.

The bone 33 is here assumed to be a femur. The abutment member 42 located in the region of the upper end 35 of the bone 33 includes a saddle-shaped bearing element 47 which is designed to engage the non-illustrated pelvis situated adjacent to the upper end 35 of the bone 33. The abutment member 44 located adjacent to the lower end 36 of the bone 33 comprises a bearing element 46 which constitutes part of an artificial knee joint.

The lower bone 9 is here provided with a prosthesis 65 which differs somewhat from the prosthesis 7 of FIG. 1. The prosthesis 65 has a shaft 64 which is again embedded in the bone 9 in a conventional manner and, as before, carries a platform 63 at its upper end. However, in contrast to the prosthesis 7, an upright projection 62 is mounted on the platform 63 of the prosthesis 65. The projection 62 is received in a passage which is formed in the bearing element 46 of the abutment member 44. The projection 62 defines a, vertical rotational axis, and the prostheses 34 and 65, as well as the bones 33 and 9, are able to rotate relative to one another about this axis.

In order to mount the prosthesis 34 in the bone 33, a longitudinal bore 37 is formed in the bone 33. The bore 37 extends throughout the length of the bone 33 and has a sufficiently large diameter to accommodate the members 42-44 and the sleeves 40, 41. The bearing element 46 of the abutment member 44 is placed in position via the lower end 36 of the bone 33. The members 42 and 43, as well as the remaining portion of the member 44, are joined and the resulting assembly is pushed into the bore 37 through the end 35 of the bone 33. The portion of the abutment member 44 which is joined to the members 42 and 43 is connected to the bearing element 46 in such a manner as to be fixed against rotation relative to the same. This may be accomplished in any conventional manner, e.g., by means of an adhesive.

The members 42-44 may be prefabricated. Joining of the members 42 and 43 to one another and to the portion of the abutment member 44 excluding the bearing element 46 may be undertaken prior to the operation.

If, during implantation of the prosthesis 34, it is found that the length of the prosthesis 34 must be better adjusted to the particular characteristics of the patient, it is possible to provide the prosthesis 34 with length adjustment section such as the sections 20 illustrated in FIG. 1 for the prosthesis 61.

Further adjustment of the prostheses 61 and 34 to the individual characteristics of a patient may be achieved by designing the prostheses 61 and 34 in such a manner that the respective pairs of proximal and distal abutment members 2, 3 and 42, 44 may have different relative angular orientations. One manner of accomplishing this is illustrated in FIGS. 3 and 4 with reference to the prosthesis 61.

Figure 3:
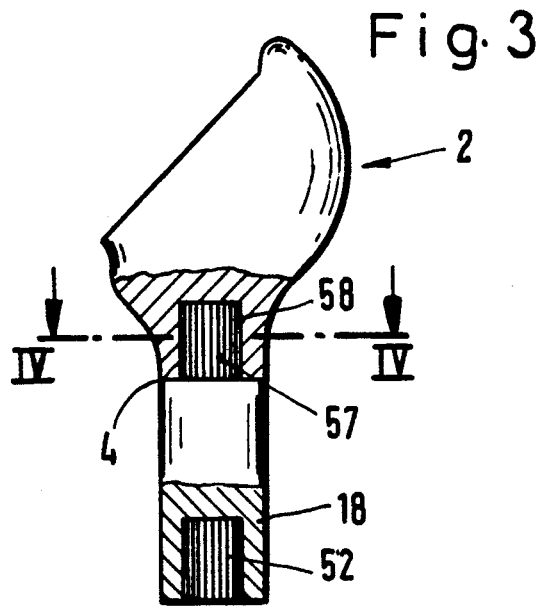
FIG. 3 is a partly sectional view illustrating one embodiment of cooperating coupling elements for joining different parts of the prostheses of FIGS. 1 and 2.
Figure 4:
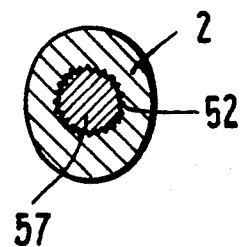
FIG. 4 is a cross-sectional view in the direction of the arrows IV—IV of FIG. 3.

FIG. 3 shows the abutment member 2 and section 18 of the prosthesis 61. Either the abutment member 2 or the section 18 is provided with an axially extending, cylindrical plug 57 while the other of the abutment member 2 and the section 18 is provided with an axially extending, cylindrical opening 58 which receives the plug 57. The plug 57 and opening 58 are centrally located. The outer periphery of the plug 57 and the inner surface of the opening 58 are provided with meshing or interengaging teeth 52. The teeth 52 prevent relative rotation of the abutment member 2 and the section 18 when the plug 57 is received in the opening 58 and thus permit the abutment member 2 and the section 18 to be fixed in different relative angular orientations. It follows that the abutment member 2 may be fixed in different angular orientations relative to the abutment member 3. The spacing between adjacent ones of the teeth 52 is preferably small so that the abutment member 2 may be adjusted relative to the section 18 in small steps. The teeth 52 enable the abutment member 2 to be angularly oriented relative to the section 18 and the abutment member 3 in accordance with the anatomical characteristics of the patient.

In the embodiment of FIG. 3, the section 18 is provided with the plug 57 while the abutment member 2 is provided with the opening 58. This is clearly seen in FIG. 4.

The sections 18-20, as well as the section 20 and the abutment member 3, may be joined to one another in the same manner as shown in FIG. 3. In this regard, FIG. 3 shows that the end of the section 18 opposite that with the plug 57 has an axially extending opening which is similar to the opening 58 and is provided with the teeth 52 internally thereof. The opening in the section 18 accommodates a mating plug on the section 19.

It will be understood that the members 42-44 of the prosthesis 34 may also be joined to one another in the manner shown in FIG. 3.

Figure 5:
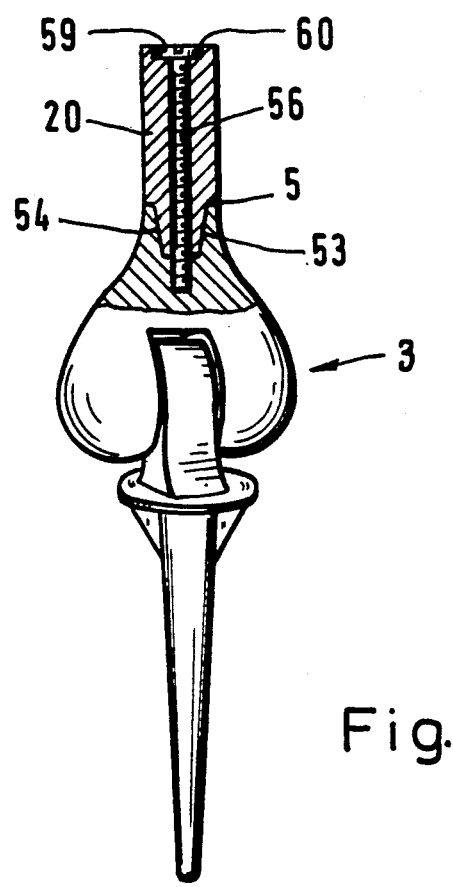
FIG. 5 is a partly sectional view illustrating another embodiment of cooperating coupling elements.

Another manner of achieving angular adjustment is illustrated in FIG. 5 which shows the abutment member 3 and section 20 of the prosthesis 61. Either the abutment member 3 or the section 20 is provided with an axially extending, conical plug 54 while the other of the abutment member 3 and the section 20 is provided with an axially extending, conical opening 53. The opening 53 is designed to mate with the plug 54. A screw 56 extends through the section 20 in axial direction of the latter and passes through the plug 54 and the opening 53. The screw 56 can freely rotate in the section 20 and threads into the abutment member 3. The end of the screw 56 remote from the abutment member 3 has a head 59 which abuts a horizontal surface 60 in the section 20 when the screw 56 is threaded into the abutment member 3. The screw 56 is tightened once the abutment member 3 and the section 20 have been properly oriented relative to one another. Tightening of the screw 56 forces the plug 54 into intimate engagement with the conical surface of the opening 53. The screw 56 is tightened until the plug 54 and the surface of the opening 53 engage one another with sufficient pressure to prevent rotation of the abutment member 3 relative to the section 20.

In the illustrated embodiment, the section 20 is formed with the plug 54 while the abutment member 3 is formed with the opening 53.

The section 20 may be joined to the section 19 by means of a conical plug and a conical opening which cooperate in the same manner as the plug 54 and the opening 53. In such a case, the end of the section 20 remote from the plug 54 is provided with a conical opening similar to the opening 53. The opening in the section 20 receives a plug on the section 19 which is similar to the plug 54. The head 59 of the screw 56 then abuts the bottom surface of the opening in the section 20 which now constitutes the horizontal surface 60. The sections 19 and 20 may be fixed against relative rotation by means other than a screw such as the screw 56. For instance, the sections 19 and 20 may be fixed relative to one another via the pin 27 and/or the pin 31.

It will be understood that the members 42-44 may also be joined to one another in the manner illustrated in and described with reference to FIG. 5.

A connection including a conical plug such as the plug 54 and a conical opening such as the opening 53 enables the prostheses 61 and 34 to be steplessly adjusted to the particular anatomical characteristics of a patient.

Another manner of joining the sections 18-20 to one another and to the abutment members 2, 3 is illustrated in FIG. 6 with reference to the sections 18, 19. One of the sections 18, 19 is provided with an axially extending opening 48 while the other of the sections 18, 19 is provided with an axially extending plug 49. In the present case, the section 18 is formed with the opening 48 while the section 19 is formed with the plug 49. The inner surface of the opening 48 is provided with threads 50 while the peripheral surface of the plug 49 is provided with threads 51 which are designed to mesh with the threads 50. The lengths of the opening 48 and the plug 49 are preferably selected in such a manner that the opening 48 is capable of accommodating the plug 49 in its entirety.

The threads 50, 51 may be fine threads. Furthermore, it is possible for the threads 50, 51 to be of the self-tightening variety in order to prevent relative rotation of the sections 18, 19. Although the threads 50, 51 may be self-tightening, auxiliary means may be provided to additionally fix the sections 18, 19 against relative rotation. For example, in addition to threads 50, 51 of the self-tightening variety, the pin 26 and/or the pin 30 may be provided to fix the sections 18, 19 relative to one another.

The members 42-44 may also be joined to one another in the manner shown in and described with reference to FIG. 6.

It is further possible to adhesively join the sections 18-20 to one another and to the abutment members 2, 3. The same applies to the members 42-44. Moreover, relative rotation of the sections 18-20 and the abutment members 2, 3 may be prevented by ultrasonically welding the sections 18-20 and the abutment members 2, 3 to one another. The members 42-44 may likewise be ultrasonically welded to one another.

The sections 18-20 and the abutment members 2, 3 may be designed as a telescopic unit as may the members 42-44. It is similarly possible for all or some of the sections 18-20, the abutment members 2, 3 and the members 42-44 to be telescopic. This permits the lengths of the prostheses 61 and 34 to be changed steplessly. Suitable means such as, for example, locking pins, may be used to prevent relative displacement of the sections 18-20 and the abutment members 2, 3, or of the members 42-44, once the prostheses 61 and 34 have been telescoped to the desired length.

The prostheses 61 and 34 may be used in all cases where a rod-like bone exhibits a defect. Although the preceding description has been primarily with reference to a defective femur, the prostheses 61 and 34 may also be used in the arm. In the event that the prosthesis 61 or 34 is used for the humerus, one of the abutment members 2, 3 or 42, 44 may at least in part constitute a shoulder joint while the other of the abutment members 2, 3 and 42, 44 may at least in part constitute an elbow joint.

The prosthesis 34 is especially well-suited for situations where at least a portion of a tubular bone can be saved. Employment of the prosthesis 34 does not require removal of bone structure since the prosthesis 34 may be mounted in a bone. This permits a maximum amount of bone which has not been destroyed by infection, trauma, tumors and so on to be retained. The retention of bone structure is important for the following reasons:

1. A bone is capable of functioning as a covering for the prosthesis 34.
2. A bone provides attachment points for tendons and muscles.
3. It is of advantage to use the natural portions of a joint which are constituted by a bone whenever and to the extent possible. In particular, significant advantages are realized by retention of the natural portions of the joint in the region of the bearing of the patella.

The sections 18-20 and the abutment members 2, 3 of the prosthesis 61 are advantageously prefabricated as are the members 42-44 of the prosthesis 34. It is of further advantage for the component parts of the prostheses 61 and 34 to be supplied in sets which contain all of the parts required by the surgeon. The sets contain parts such as the section 20 which enable length adjustments, including adjustments for conventional manufacturing tolerances, to be made. These adjusting parts are used by the surgeon to fit the prosthesis 61 or 34 to the individual characteristics of the patient.

As indicated previously, the abutment members 2, 3 and 42, 44 may be prefabricated. The distal abutment member 3 or 44 may be designed as part of an artificial knee joint which is capable of undergoing rotation about a horizontal and/or vertical axis. The distal abutment member 3 or 44 may also be designed as a replacement for the condyle. It is further possible to design the distal abutment member 3 or 44 in such a manner that it constitutes part of an artificial knee joint capable of undergoing rotation about a horizontal and/or vertical axis and additionally serves as a replacement for the condyle. Another alternative is to design the abutment member 3 or 44 so that it constitutes part of an artificial knee joint and to provide a discrete replacement for the condyle which may be slidably mounted on the abutment member 3 or 44. An abutment member 3 or 44 constituting part of an artificial knee joint may also include a replacement for the bearing of the patella or, alternatively, replacements for both the condyle and the bearing of the patella.

The invention enables the surgeon to have at his disposal an optimum building system which permits significant savings in both manufacture and installation to be realized. For example, it is possible to construct a prosthesis 61 or 34 having a basic abutment member 3 or 44. By appropriate design of the abutment member 3 or 44 and suitable selection of the parts of the building system, a replacement for the condyle and/or a replacement for the bearing of the patella may subsequently be mounted on the abutment member 3 or 44 if necessary.

As outlined previously, the prostheses 61 and 34 may be used in the arm. In the event that the prosthesis 61 or 34 is used for the humerus, the abutment member 2 or 42 may be designed so as to constitute part of an artificial shoulder joint while the abutment member 3 or 44 may be designed in such a manner as to constitute part of an artificial elbow joint.

The prostheses may be made of metal. A cobalt-chromium-molybdenum alloy may be used for the prosthesis 61 or 34 and, in particular, the cobalt-chromium-molybdenum alloy known as Vitalium in the medical industry.

The prostheses 61 and 34 may also be made of a titanium alloy. When a titanium alloy is used, however, it is preferred that the bearing elements at an artificial hip joint be composed of or coated with a material other than a titanium alloy. With reference to the abutment member 2 of the prosthesis 61, the ball 11 is preferably composed of a ceramic instead of titanium and the socket 10 is preferably composed of polyethylene instead of titanium.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. An internal push-through prosthesis for performing the load-bearing function of a tubular bone between two joints, particularly the load-bearing function of a femur, which is capable of covering a portion of the prosthesis at least in the region of one of the joints, comprising an elongated variable-length bridging member having first and second ends and a portion of said bridging member being arranged to extend through the tubular bone upon implantation of the prosthesis, said bridging member comprising a plurality of separable sections disposed end-to-end and joining means for separably connecting said sections to each other, adjacent ones of said sections being provided with cooperating tapering joining elements; a first abutment member at said first end and constituting at least a portion of a first artificial joint; a second abutment member arranged to be mounted at said second end and constituting at least a portion of a second artificial joint; and means for joining at least one of said abutment members to the respective end of said bridging member in any one of a plurality of different angular positions relative to said bridging member.

2. The prosthesis of claim 1, wherein said joining elements are substantially conical.

3. The prosthesis of claim 1, comprising a compression element for urging said joining elements into engagement with one another.

4. The prosthesis of claim 3, wherein said compression element comprises a screw which extends through said joining elements in axial direction thereof.

5. An internal prosthesis for full replacement of a bone shaft, comprising a rod-like bridging member designed to span at least part of the gap between two joints of the anatomy, said bridging member including at least one adjusting section for adjusting the length thereof and said bridging member having longitudinally spaced-apart first and second ends; a first abutment member arranged to be mounted at said first end and at least in part constituting a first artificial joint; a second abutment member arranged to be mounted at said second end and at least in part constituting a second artificial join; and means for joining at least one of said abutment members to said bridging member so as to permit said at least one abutment member to be fixed in any one of a plurality of different angular positions relative to said bridging member, said joining means including a socket in said bridging member, a plug provided on said at least one abutment member and rotatably received in said socket, and a locking element arranged to extend transversely of and to engage said plug so as to lock said bridging member and said at least one abutment member against relative rotation as well as against relative movement axially of said bridging member.

6. An internal push-through prosthesis for performing the load-bearing function of a tubular bone between two joints, particularly the load-bearing function of a femur, which is capable of covering a portion of the prosthesis at least in the region of one of the joints, comprising an elongated bridging member having first and second ends and a portion of said bridging member being arranged to extend through the tubular bone upon implantation of the prosthesis; a first abutment member at said first end and constituting at least a portion of a first artificial joint; a second abutment member arranged to be mounted at said second end and constituting at least a portion of a second artificial joint; means for joining at least one of said abutment members to the respective end of said bridging member in any one of a plurality of different angular positions relative to said bridging member, said joining means comprising a socket and a plug rotatable in said socket; and means for locking said bridging member and at least one of said abutment members against relative movement longitudinally of said bridging member, said locking means including a locking element arranged to extend transverse to and engage said plug.

* * * * *